United States Patent [19]

O'Neill

[11] Patent Number: 5,672,289
[45] Date of Patent: Sep. 30, 1997

[54] HEATER CONTROL CIRCUIT

[75] Inventor: Michael J. O'Neill, Shoreham, Vt.

[73] Assignee: The Perkin-Elmer Corporation, Norwalk, Conn.

[21] Appl. No.: 599,410

[22] Filed: Jan. 11, 1996

[51] Int. Cl.⁶ .................................................. H05B 1/02
[52] U.S. Cl. ........................... 219/497; 219/505; 219/209; 374/11; 374/33
[58] Field of Search .................................. 219/494, 499, 219/497, 501, 503, 505, 508, 209, 210; 374/11, 33, 10, 12, 13

[56] References Cited

U.S. PATENT DOCUMENTS

| | | | |
|---|---|---|---|
| 3,643,491 | 2/1972 | Dell et al. | 73/15 B |
| 3,675,465 | 7/1972 | Sommer et al. | 73/15 B |
| 4,040,288 | 8/1977 | Kotelnikov et al. | 73/15 B |
| 4,985,683 | 1/1991 | O'Neill | 328/133 |
| 5,098,196 | 3/1992 | O'Neill | 374/11 |
| 5,439,291 | 8/1995 | Reading | 374/11 |

*Primary Examiner*—Mark H. Paschall
*Attorney, Agent, or Firm*—Edwin T. Grimes; David Aker

[57] ABSTRACT

A Control circuit for a differential scanning calorimeter which includes a sample heater, a reference heater, a system for generating a sample heater DC voltage and a system for generating a reference heater DC voltage. A balanced operational amplifier arrangement is provided which includes a circuit for controlling the differential heater voltage and a circuit for independently controlling the average heater voltage, so that the average heater power and the differential heater power are independently controlled.

6 Claims, 2 Drawing Sheets

HEATER CONTROL CIRCUIT

FIELD OF INVENTION

This invention relates to calorimetric analytical instruments, and more particularly to a heater control circuit for a differential scanning calorimeter.

BACKGROUND OF THE INVENTION

Differential thermal techniques generally consist of applying heat simultaneously to a sample material and a reference material and measuring a parameter, such as differential power input, as the sample goes through a physical or chemical change. In differential scanning calorimetry (DSC), differential power between the sample and reference is measured. The differential power represents the difference in energy required to maintain the sample and reference in accord with a heating or cooling program.

In prior art DSC instruments, the heaters were driven in a time-division multiplexed mode. For approximately one-half of the time the heaters supplied average power in order to maintain the average temperature of the sample holders at the set-point temperature, while for the remainder of the time the heaters were driven in such a way as to provide differential power, in order to null the temperature difference between the sample holders. The multiplexing was done at a high enough frequency, typically 600 Hz, so that the AC components of the heater power were effectively eliminated by the thermal time constant of the sample holder.

The prior art arrangement had a number of disadvantages. A transformer coupling was required for the differential power control, and accurately matched power rectifiers were required for the average power control circuit. There was also the problem of AC coupling between the high-voltage heater wiring and the low-noise temperature-sensing circuit.

In addition, since the sensors are necessarily configured in an AC bridge circuit, which obviously must operate at a frequency different from the heater drive frequency, it was necessary to demodulate the two temperature error signals, provide low-pass filtering, and then modulate the error signals at the heater frequency.

SUMMARY OF THE INVENTION

An object of the invention is to overcome or reduce the disadvantages of the prior art instruments.

Another object of the invention is to generate sample heater voltage and reference heater voltage in a differential scanning calorimeter in such a way that average heater power and differential heater power are accurately and independently controlled.

The foregoing and other objects are achieved by the provision of a new and improved control circuit for a differential scanning calorimeter instrument which includes sample heater means, reference heater means, means for generating a sample heater DC voltage and means for generating a reference heater DC voltage. A balanced operational amplifier arrangement is provided which includes means for controlling differential heater voltage and means for independently controlling average heater voltage, whereby average heater power and differential heater power are independently controlled.

According to one aspect of the invention, means are provided for measuring differential power.

According to another aspect of the invention, means are provided for controlling minimum heater power.

This new and improved heater control circuit eliminates the prior art requirements for a transformer and matched rectifiers, and the requirement for modulation of the error signals at the heater frequency, and relaxes the specification for unwanted AC signal coupling between heater and sensor circuits.

There has thus been outlined rather broadly the more important features of the invention in order that the detailed description thereof that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis for the designing of other circuitry for carrying out the purposes of the invention. It is important, therefore, that this disclosure be regarded as including such equivalent circuitry as do not depart from the spirit and scope of the invention.

Several embodiments of the invention have been chosen for purposes of illustration and description, and are shown in the accompanying drawings forming a part of the specification, wherein:

FIG. 1 is a simplified vertical sectional view of a portion of an analytical instrument incorporating the invention; and FIG. 2 is a schematic diagram of a circuit according to the invention.

DETAILED DESCRIPTION OF A PRESENTLY PREFERRED EMBODIMENT OF THE INVENTION

Figure 1:
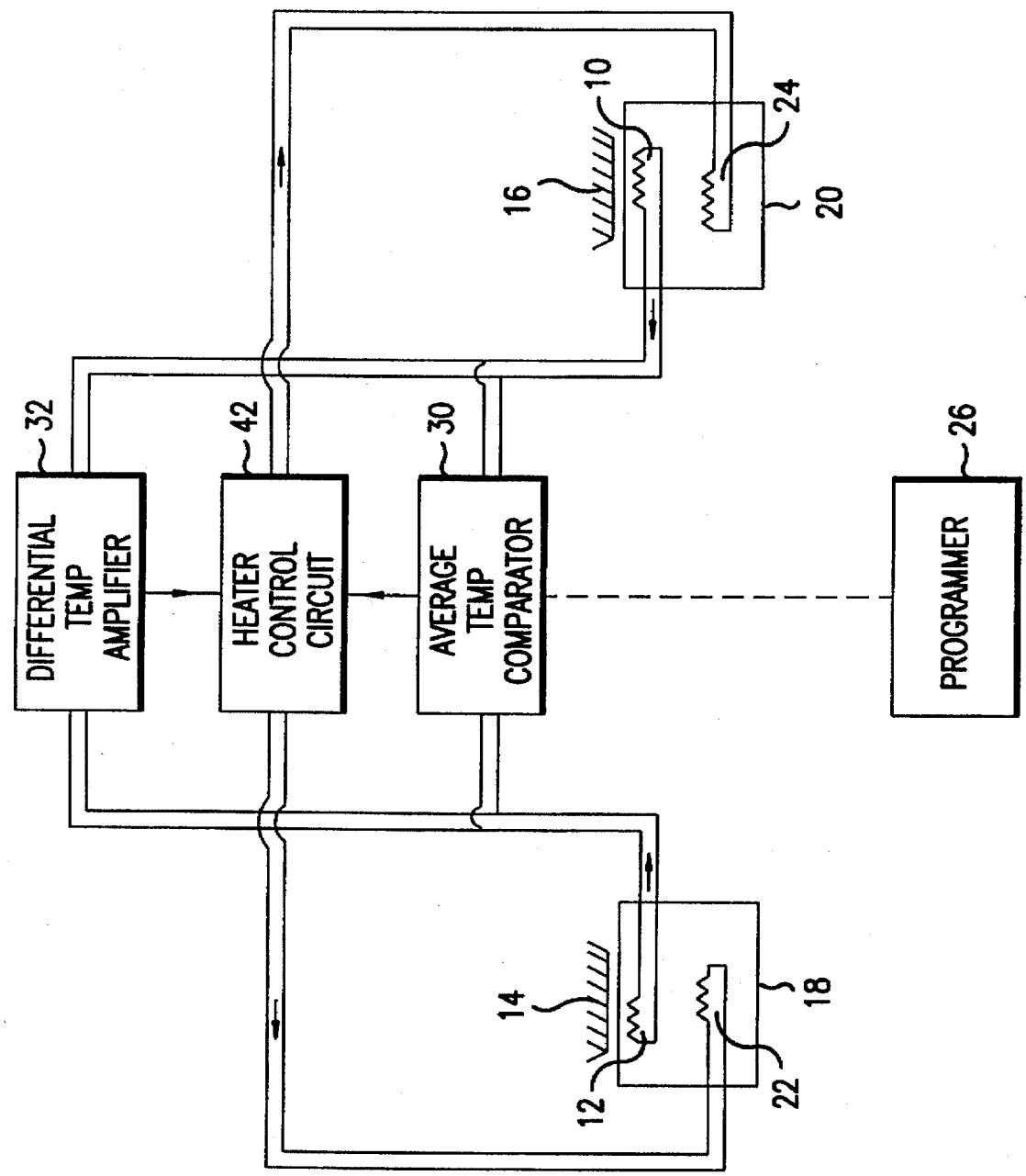

FIG. 1 illustrates a portion 10 of a DSC, which can be used to implement the present invention. This instrument measures the differential power required to keep both sample and reference sensors 10, 12 at the same temperature throughout the DSC experiment. The apparatus, as illustrated, is described and explained in basic terms in E. S. Watson et al., "A Differential Scanning Calorimeter for Quantitative Differential Analysis", Anal. Chem. 36(7), 1233–1238 (1964), which is incorporated herein by reference.

In FIG. 1, reference and sample containers 14 and 16, respectively, are mounted on platforms 18 and 20. The reference generally is a standard (or simply the empty container) and the sample is a material having some characteristic parameter such as specific heat to be compared with that of the standard.

The reference 14 and the sample 16 are subjected to a programmed heating or cooling program, in accord with a prescribed function, through a process of programmed and balanced heating. The programmed heating or cooling run subjects the sample and reference to an externally applied disturbance such as heat which induces a change in temperature.

Both the programmed heating and the balanced heating are performed through the reference heater 22 and the sample heater 24 in the reference and sample bases 18 and 20. The system of FIG. 1 is divided into two separate control loops, one loop for average temperature control and the other for differential temperature control. In the average temperature control loop, the programmer 26 provides a signal which is proportional to the desired temperature of the sample holder 16 and the reference holder 14. The programmer signal is compared in the average temperature comparator 30 with signals received from resistance thermometers 12 and 10. If the average temperature is greater than the temperature called for by the programmer 26, then the power supply to the sample and reference heaters 24, 22 is decreased, and vice versa if the average temperature is less than that called for by the programmer 26. This is effected through heater control circuit 42, which receives the average temperature error signal (TP-TAV) from the average temperature comparator 30 and provides driving signals to the sample and reference heaters 24, 22.

In the differential temperature control loop, temperature signals received from the resistance thermometers 10, 12 are relayed to the differential temperature amplifier 32. The differential temperature amplifier 32 responds to a disparity in the sample and reference temperature signals by adjusting the differential power increment fed to the sample and reference heaters 24,22 to correct the temperature difference. This is effected through heater control circuit 42, which receives the (dT) error signal (TS-TR) from the differential temperature amplifier 32 and provides driving signals to the sample and reference heaters 24, 22.

Figure 2:
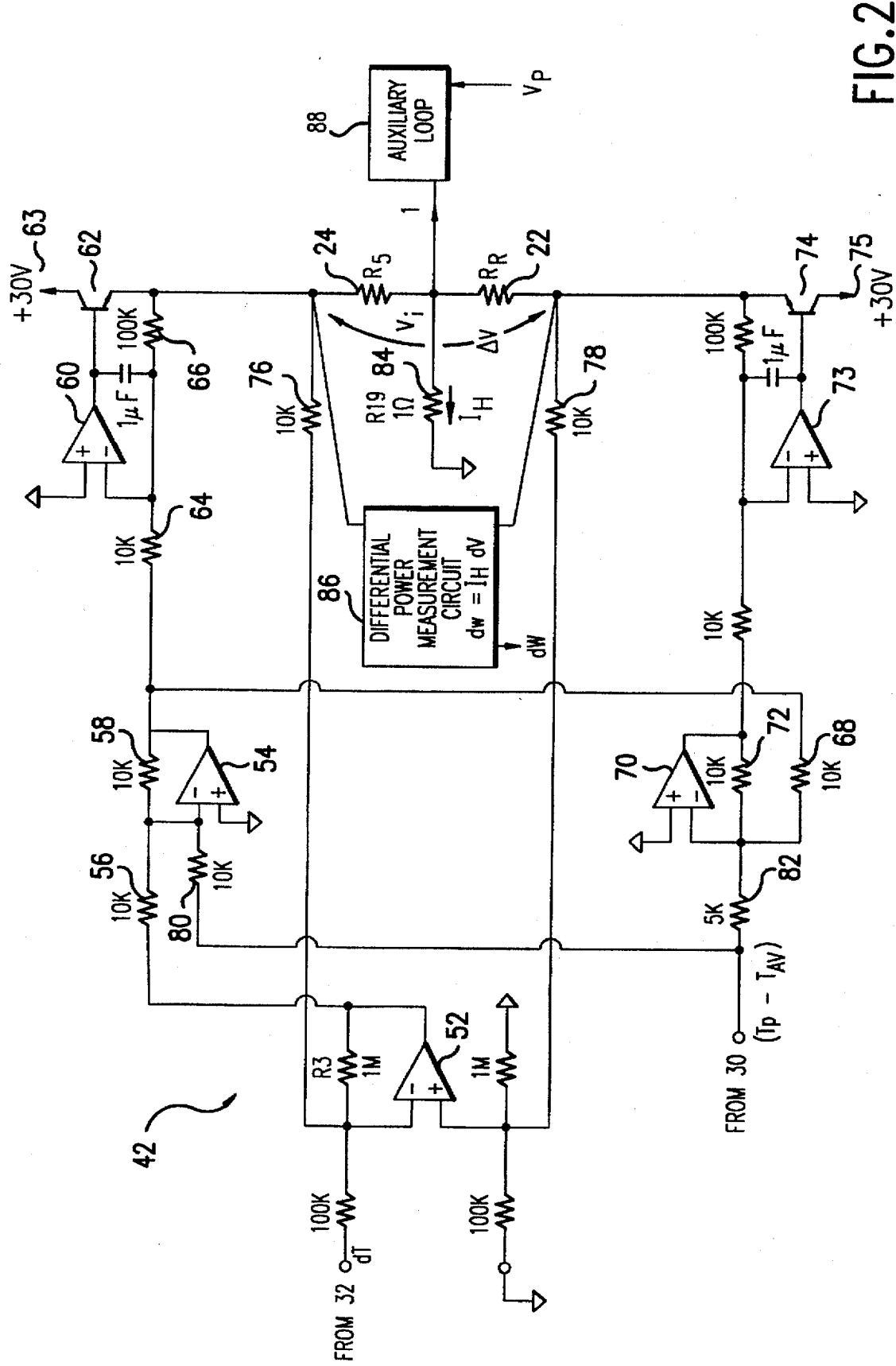

FIG. 2 is a diagram illustrating circuitry 42 of the invention.

Differential Heater Voltage Control

The (dT) error signal (TS-TR) from the differential temperature amplifier 32 is applied to the inverting input of a first or instrumentation amplifier 52, with the other input grounded. The output of the first amplifier 52 is inverted by a second amplifier 54 with a gain of −1, as determined by resistors 56 and 58, and the output of this second amplifier is amplified by a fourth amplifier 60 and power transistor 62 with a gain of −10, as determined by resistors 64 and 66. The power transistor 62 has a (+30 V) voltage input 63. The output voltage from this stage appears across the sample heater (RS) 24.

The output voltage from the second amplifier 54 is also applied through resistor 68 to a third or inverting amplifier 70, with a gain of −1, as determined by resistors 72 and 68, and the output of the third amplifier 70 is applied to an output stage comprising a fifth amplifier 73 and a second power transistor 74, with a gain of −10, which drives the reference heater (RR) 22. The second power transistor 74 has a (+30 V) voltage input 75. Thus, the sample heater voltage is (+10) times the output voltage of the first amplifier 52, while the reference heater voltage is (−10) times this voltage. The voltage gain from the (dT) input terminal 32 to the heaters 22 and 24 is determined by the overall negative feedback through resistors 76 and 78. As a result, if the input voltage is +1 V, the sample and reference heaters 24 and 22 are driven at −0.05 V and +0.05 V, respectively, with respect to their average voltage. It will be appreciated that the circuit as shown cannot supply negative voltages to the heaters. As will be discussed more fully hereinafter, the heaters are always driven at a positive average voltage, and the circuit described above provides a differential heater voltage, and thus generates differential heater power.

Average Heater Voltage Control

The average temperature error signal (TP-TAV), where (TP) is the preset temperature and (TAV) is the average temperature, from average temperature computer 30, is applied through resistors 80 and 82 to the second and third amplifiers 54 and 70. The gain of the second amplifier 54 is (−1), as determined by resistors 58 and 80, and thus the voltage gain from the input to the sample heater 24 is (+10).

The gain of the third amplifier 70 with respect to the input signal is (−2) as determined by resistors 72 and 82. However, the additional input to the third amplifier 70 from the second amplifier 54, via resistor 68, effectively cancels half of this gain, so that the outputs of the second and third amplifiers 54 and 70 are equal, and as a result the voltage gain to both heaters 24 and 22 is (+10).

An essential feature of the average heater control system is that there is a very small differential power component associated with the average power. In the circuit described herein, all the resistors have a tolerance of 0.1%, and therefore there could be a voltage gain mismatch of 0.8% in the worst case. However, the differential voltage control loop, with a loop gain of 2000, reduces the heater voltage mismatch to negligible proportions.

Differential Power Measurement

To determine the differential power (dW) generated in the heaters, a circuit 86 is provided to multiply the total heater current (IH) by the differential heater voltage (dV):

$$dW = I_H dV$$

Resistor 84 is a one-ohm current-monitoring resistor, developing a voltage (VI) proportional to heater current. After amplification by a factor of 10, this voltage is converted to digital form, and multiplied in firmware by a voltage proportional to the differential temperature error signal, which in turn is proportional to differential heater voltage.

Minimum Heater Power Control

In prior art instruments, differential power control was completely independent of the average power control system. Thus, it was possible to disable the latter entirely, for instance by attempting to program the average temperature down at a rate greater than the natural cooling rate of the sample holders, without affecting the measurement of differential power.

According to the system of the present invention, without multiplexing, the heaters cannot be allowed to turn off, since this would disable the differential power control system. Therefore an auxiliary loop 88 is enabled whenever the heater current, as measured by (VI), decreases to a preset value (VP). This loop maintains this preset value of heater current until the average temperature falls below the set point temperature (TP) when the main loop is enabled again.

Although particular embodiments of the invention are herein disclosed for purposes of explanation, various modifications thereof, after study of this specification, will be apparent to those skilled in the art to which the invention pertains.

What is claimed is:

1. A control circuit for a differential scanning calorimeter comprising, in combination, sample heater means, including means for generating a sample heater DC voltage;

reference heater means, including means for generating a reference heater DC voltage;

means for measuring a difference voltage between said sample heater DC voltage and said reference heater DC voltage;

means for measuring an average voltage of said sample heater DC voltage and said reference heater DC voltage; and a heater control circuit including means for independently controlling said differential heater voltage in response to said difference voltage and means for independently controlling said average heater voltage in response to said average voltage.

2. The apparatus of claim 1 further comprising means for measuring differential power.

3. The apparatus of claim 1 further comprising means for setting said sample heater DC voltage and said reference heater DC voltage to a minimum level.

4. The apparatus of claim 1 wherein said means for controlling differential heater voltage comprises first amplifier means having an inverting input for receiving a differential temperature error signal, second amplifier means for receiving an inverting output from the first amplifier means, fourth amplifier means for amplifying output from the second amplifier means, said means for generating a sample heater voltage including a first power transistor means for receiving output from said fourth amplifier means and outputting a voltage across said sample heater; a third inverting amplifier for receiving output voltage from said second amplifier, a fifth amplifier for receiving output from said third amplifier, said means for generating a reference heater voltage including a second transistor for receiving output from said fifth amplifier and outputting a voltage across said reference heater.

5. The apparatus of claim 4 wherein said second amplifier means receives an average temperature error signal and said third amplifier means receives said average temperature error signal, an output of the second amplifier means is connected to the input of the third amplifier means to cancel one half the gain of the third amplifier means so that the outputs of the second and third amplifier means are equal, whereby the voltage gain to both of said heater means is equal.

6. The apparatus of claim 1 herein the heater control circuit comprises a balanced operational amplifier.

* * * * *